US00PP08339P

United States Patent [19]

Marciel et al.

[11] Patent Number: Plant 8,339

[45] Date of Patent: Aug. 10, 1993

[54] HYBRID TEA ROSE PLANT NAMED DEVFRAGO

[75] Inventors: Stanley G. Marciel; Jeanne A. Marciel, both of Aptos, Calif.

[73] Assignee: DeVor Nurseries, Inc., Watsonville, Calif.

[21] Appl. No.: 919,368

[22] Filed: Jul. 23, 1992

[51] Int. Cl.[5] ..... A01H 5/00

[52] U.S. Cl. ..... Plt./16

[58] Field of Search ..... Plt./11, 16

*Primary Examiner*—Howard J. Locker

*Attorney, Agent, or Firm*—Christie, Parker & Hale

[57] ABSTRACT

A new variety of hybrid tea rose plant producing apricot flowers.

1 Drawing Sheet

SUMMARY OF THE INVENTION

The present invention relates to a new and distinct variety of rose plant of the hybrid tea rose class, which was originated by my crossing as seed and pollen parents two unnamed and unpatented seedlings of our creation. The varietal denomination of this new rose is 'Devfrago'.

Among the novel characteristics possessed by this new variety which distinguishes it from its parents and all other varieties of which I am aware is its attractive apricot flower coloration.

Asexual reproduction by propagation by budding of the new variety as performed in Watsonville, Calif. shows that the foregoing and other distinguishing characteristics come true to form and are established and transmitted through succeeding propagations.

BRIEF DESCRIPTION OF ILLUSTRATION

The accompanying illustration shows typical specimens of the flowers and vegetative growth of the new variety depicted in color as nearly true as it is reasonably possible to make the same in a color illustrations of this character. Phenotypic expression, including colors, may vary depending upon growing conditions, such as climate, soil, and cultivation conditions.

DETAILED DESCRIPTION OF THE NEW VARIETY

The following is a detailed description of my new variety, with color terminology in accordance with The Royal Horticultural Society Colour Chart (R.H.S.C.C.). The terminology used in the color descriptions herein refers to plate numbers in the aforementioned color chart.

Parentage: Seedling.

*Seed parent.*—Unnamed seedling.

*Pollen parent.*—Unnamed seedling.

Class: Hybrid Tea.

The following further horticultural observations were made of specimens grown in greenhouses in Watsonville, Calif. in the months of January and February.

FLOWER

Blooming habit: Recurrent.

A. Bud:

(1) *Size.*—Small.

(2) *Form.*—Slender — tapering.

(3) *Color.*—As sepals first divide, near 31C to 40C with some reddish flush; base of petal near 22A.

(4) *Sepals.*—Longer than bud. Five single sepals, three narrow pointed, some slightly foliated.

(5) *Peduncle.*—Length — about 7.5 to 13 cm. Aspect — slightly curved. Strength — sturdy and erect. Color — near 144C.

(6) *Bracts.*—Number — 1 or 2. Color — near 139A. Form — broadly elliptical with long apex, margin ciliate. Location in relation to flower — approximately 10 cm. from bloom.

B. Bloom:

(1) *Size.*—Average size when fully expanded — about 11 to 13 cm.

(2) *Borne.*—Singly.

(3) *Form.*—High centered at first; becoming flat when fully opened.

(4) *Petalage.*—Number of petals under normal conditions — about 26 to 30.

(5) *Color.*—After sepals fall and petals begin to unfurl, outer petals top surface is near 20C with near 20A at petal base; petal undersurface is deeper toned at central portion, near 20A, and paler toward petal edge. Some outer petals have reddish flush. As flower opens, predominant flower coloration viewed from above is near 25D to 25C. Base of petals near point of petal attachment is near 3A. General tonality from a distance is pleasing apricot coloring. Upon aging, flower tonality tends toward gold and pink flush appears more pronounced on outer petals. Petal coloration generally lightens.

C. Petals:

(1) *Texture.*—Medium thick.

(2) *Appearance.*—Ribbed appearance inside because of veining but feels smooth to the touch; outside resembles soft leather.

(3) *Form.*—Broad obovate.

(4) *Arrangement.*—Imbricated.

(5) *Petaloids in center.*—Few.

(6) *Persistence.*—Drop off cleanly.

(7) *Fragrance.*—Very strong, heavy sweet fragrance.

(8) *Lasting quality.*—Long lasting on plant, about 7 to 8 days as a cut flower.

REPRODUCTIVE ORGANS

A. Stamens, filaments and anthers:

*Arrangement and color.*—Introrse, regularly arranged around styles.

B. Anthers:

*Color.*—Near 17C on edges, slightly lighter in center.

C. Filaments:

*Color.*—Near 14B; stamens near 16A.

D. Pollen:

*Color.*—Near 17C.

E. Styles:

*Color.*—Near 150C. Bunched, uneven lengths, medium thin to slightly thick.

F. Stigmas: Near 23B.

G. Hips:

*Shape.*—Globular.

*Size.*—About 2.7 to 3 cm. in width and about 3 cm. in length. Seeds protrude on about ½ of the hips.

PLANT

A. Form: Upright, bushy.

B. Growth: Vigorous, uniform branching.

*Height attained.*—About 140 cm.

C. Foliage: Compound 3, 5 and 7 leaflets.

(1) *Size.*—Large.

(2) *Quantity.*—Abundant.

(3) *Color.*—New foliage: Upper side — near 147A. Under side — near 147B. Old foliage: Upper side — near 137A. Under side — near 138A.

(4) *Shape.*—Oval.

(5) *Texture.*—Upper side is pinnately veined — scabrous; underside is pinnately veined — scurfy.

(6) *Edge.*—Serrated.

(7) *Serration.*—Normal.

(8) *Leaf stem.*—Color — near 148B with underside near 137C.

(9) *Stipules.*—Medium length, adnate with auricles facing outwards, auricles are barbed.

(10) *Auricle description.*—Slender with red/purple barbs.

(11) *Resistance to disease.*—Blackspot — under greenhouse conditions no blackspot. Mildew — good resistance. Rust — under greenhouse conditions no rust.

D. Wood:

(1) *New wood.*—Color — near 183A. Bark — smooth.

(2) *Old wood.*—Color — near 137C. Bark — smooth.

(3) *Flower stem length from last cutting.*—About 51 to 61 cm. leaving 1 to 5 leaves after cutting.

E. Thorns:

(1) *Thorns.*—Quantity (main stalk) — few. On laterals from stalk — few. Form — thin, curved downwardly. Length — medium. Color — near 183C, very tip is near 162B. Position — irregular.

(2) *Prickles.*—Average.

F. Winter hardiness: Wintered well in Watsonville, Calif.

I claim:

1. A new and distinct variety of rose plant of the hybrid tea rose class, substantially as shown and described.

* * * * *

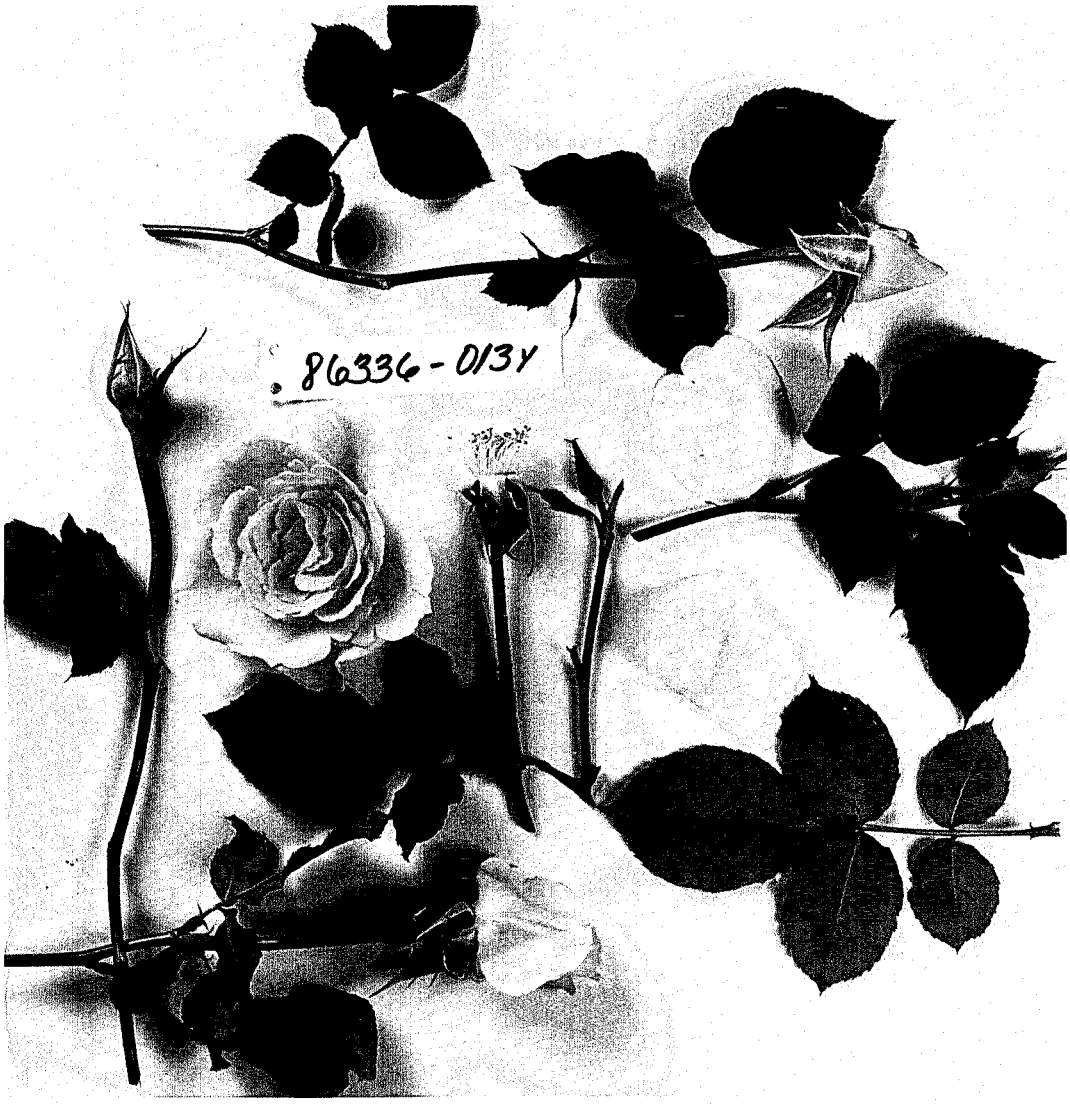
86336-013Y